(12) United States Patent
Kim et al.

(10) Patent No.: US 10,489,902 B2  
(45) Date of Patent: Nov. 26, 2019

(54) INSPECTION APPARATUS, SEMICONDUCTOR DEVICE MANUFACTURING SYSTEM INCLUDING THE SAME, AND METHOD OF MANUFACTURING A SEMICONDUCTOR DEVICE USING THE SAME

(71) Applicant: SAMSUNG ELECTRONICS CO., LTD., Suwon-si, Gyeonggi-Do (KR)

(72) Inventors: Kwang Soo Kim, Pyeongtaek-si (KR); Sangbong Park, Yongin-si (KR); Byeonghwan Jeon, Yongin-si (KR); Youngduk Kim, Seongnam-si (KR)

(73) Assignee: SAMSUNG ELECTRONICS CO., LTD., Suwon-Si, Gyeonggi-Do (KR)

(*) Notice: Subject to any disclaimer, the term of this patent is extended or adjusted under 35 U.S.C. 154(b) by 315 days.

(21) Appl. No.: 15/247,537

(22) Filed: Aug. 25, 2016

(65) Prior Publication Data  
US 2017/0116727 A1 Apr. 27, 2017

(30) Foreign Application Priority Data  
Oct. 21, 2015 (KR) .................. 10-2015-0146727

(51) Int. Cl.  
*G06T 7/00* (2017.01)  
*G01N 21/95* (2006.01)  
(Continued)

(52) U.S. Cl.  
CPC ....... *G06T 7/0008* (2013.01); *G01N 21/9501* (2013.01); *G01N 21/95623* (2013.01);  
(Continued)

(58) Field of Classification Search  
CPC .......... H01L 22/12; H01L 2924/00014; H01L 2924/0002; H01L 22/20; H01L 2924/00; H01L 22/26; H01L 21/67288; H01L 2224/05599; H01L 2224/45099; H01L 2224/85399; H01L 22/14; H01L 23/544;  
(Continued)

(56) References Cited

U.S. PATENT DOCUMENTS

| | | | | |
|---|---|---|---|---|
| 5,136,149 A | * | 8/1992 | Fujiwara | G02B 7/32 250/201.5 |
| 5,177,559 A | * | 1/1993 | Batchelder | G01N 21/95623 356/237.5 |
| 5,264,912 A | * | 11/1993 | Vaught | G01N 21/94 250/550 |
| 6,429,943 B1 | * | 8/2002 | Opsal | G01B 11/02 356/625 |

(Continued)

FOREIGN PATENT DOCUMENTS

KR 1020110119082 11/2011

*Primary Examiner* — Dave Czekaj  
*Assistant Examiner* — Kehinde Abimbola  
(74) *Attorney, Agent, or Firm* — F. Chau & Associates, LLC

(57) ABSTRACT

An inspection apparatus includes a light source device providing incident light to a substrate, an objective lens receiving reflection light reflected from the substrate, a light splitting device disposed over the objective lens, first and second optical sensors disposed at both sides of the light splitting device, respectively, and first and second spatial filters disposed between the first optical sensor and the substrate and between the second optical sensor and the substrate, respectively. The first and second spatial filters transmit the reflection light in different forms from each other.

18 Claims, 12 Drawing Sheets

(51) Int. Cl.
*G01N 21/956* (2006.01)
*G02B 13/00* (2006.01)
*G02B 27/09* (2006.01)
*G02B 27/14* (2006.01)
*H01L 21/66* (2006.01)
*H01L 21/67* (2006.01)
*H04N 5/247* (2006.01)

(52) U.S. Cl.
CPC ..... *G02B 13/0095* (2013.01); *G02B 27/0988* (2013.01); *G02B 27/14* (2013.01); *G06T 7/001* (2013.01); *H01L 21/67276* (2013.01); *H01L 22/12* (2013.01); *H04N 5/247* (2013.01); *G01N 2201/061* (2013.01); *G06T 2207/20224* (2013.01); *G06T 2207/30148* (2013.01)

(58) Field of Classification Search
CPC ................. H01L 21/304; H01L 21/78; H01L 2223/54426; H01L 22/24
USPC .......................................................... 348/87
See application file for complete search history.

(56) References Cited

U.S. PATENT DOCUMENTS

| | | | |
|---|---|---|---|
| 7,075,076 B2 | 7/2006 | Makino et al. | |
| 7,138,619 B1 | 11/2006 | Ferrante et al. | |
| 7,176,433 B1 | 2/2007 | Rosengaus | |
| 7,345,754 B1 * | 3/2008 | Zhao | G01N 21/4738 356/237.1 |
| 7,623,229 B1 * | 11/2009 | Vaez-Iravani | G01N 21/9501 356/237.4 |
| 8,400,710 B2 * | 3/2013 | Terakawa | G01N 21/4738 359/389 |
| 8,605,275 B2 | 12/2013 | Chen et al. | |
| 8,831,334 B2 | 9/2014 | Luo et al. | |
| 9,442,077 B2 * | 9/2016 | Huang | G01N 21/9501 |
| 2002/0162979 A1 * | 11/2002 | Kusunose | G01N 21/8901 250/559.45 |
| 2004/0178727 A1 * | 9/2004 | Song | H05B 33/04 313/512 |
| 2004/0179727 A1 * | 9/2004 | Takeuchi | G01N 21/95607 382/145 |
| 2012/0133762 A1 | 5/2012 | Schweitzer et al. | |
| 2012/0155740 A1 | 6/2012 | Cho et al. | |
| 2012/0287263 A1 | 11/2012 | Zhou | |
| 2015/0063677 A1 * | 3/2015 | Huang | G01N 21/9501 382/149 |

* cited by examiner

INSPECTION APPARATUS, SEMICONDUCTOR DEVICE MANUFACTURING SYSTEM INCLUDING THE SAME, AND METHOD OF MANUFACTURING A SEMICONDUCTOR DEVICE USING THE SAME

CROSS-REFERENCE TO RELATED APPLICATION

This U.S. non-provisional patent application claims priority under 35 U.S.C. § 119 to Korean Patent Application No. 10-2015-0146727, filed on Oct. 21, 2015, in the Korean Intellectual Property Office, the disclosure of which is incorporated by reference in its entirety herein.

BACKGROUND

1. Technical Field

Embodiments of the inventive concepts relate to a system of manufacturing a semiconductor device and a method of manufacturing a semiconductor device using the same. More particularly, embodiments of the inventive concept relate to an inspection apparatus used for detecting a defect on a substrate, a manufacturing system including the same, and a method of manufacturing a semiconductor device using the same.

2. Discussion of Related Art

Semiconductor devices are electronic components that exploit the electronic properties of semiconductor materials such as silicon, germanium, gallium arsenide, and organic semiconductors. Semiconductor devices are manufactured both as single discrete devices and as integrated circuits. Semiconductor devices may be used as components of telecommunications equipment. High-performance and highly-integrated semiconductor devices are needed in view of the rapid development of the telecommunications field. However, it is difficult to improve a production yield of apparatuses that manufacture such high-performance and highly-integrated semiconductor devices.

SUMMARY

At least one embodiment of the inventive concept may provide an inspection apparatus capable of detecting a defect in real time, a manufacturing system including the same, and a method of manufacturing a semiconductor device using the same.

At least one embodiment of the inventive concept may also provide an inspection apparatus capable of detecting a defect using a single scan, a manufacturing system including the same, and a method of manufacturing a semiconductor device using the same.

According to an exemplary embodiment of the inventive concept, an inspection apparatus includes a light source device for providing incident light to a substrate, an objective lens for transmitting reflection light reflected from the substrate, a light splitting device disposed over the objective lens for receiving the reflection light transmitted from the objective lens, the light splitting device for splitting the received reflection light into first and second split light, a first optical sensor disposed at one side of the light splitting device for detecting the first split light, a second optical sensor disposed at a second other side of the light splitting device for detecting the second split light, a first spatial filtering device disposed between the first optical sensor and the light splitting device and including a first spatial filter, and a second spatial filtering device disposed between the second optical sensor and the light splitting device and including a second spatial filter. The first and second spatial filters have shapes different from each other.

According to an exemplary embodiment of the inventive concept, a system of manufacturing a semiconductor device includes a manufacturing apparatus for performing a manufacturing process on a substrate to generate a semiconductor device, and an inspection apparatus spaced apart from the manufacturing apparatus for inspecting the substrate. The inspection apparatus includes a light source device for providing incident light to the substrate, an objective lens for transmitting reflection light reflected from the substrate, a light splitting device disposed over the objective lens for receiving the reflection light transmitted from the objective lens, the light splitting device for splitting the received reflection light into first and second split light, a first optical sensor disposed at one side of the light splitting device for detecting the first split light, a second optical sensor disposed at a second other side of the light splitting device for detecting the second split light, a first spatial filtering device disposed between the first optical sensor and the light splitting device and including a first spatial filter, and a second spatial filtering device disposed between the second optical sensor and the light splitting device and including a second spatial filter. The first and second spatial filters have shapes different from each other.

According to an exemplary embodiment of the inventive concept, an inspection apparatus includes a light source device for providing incident light to a substrate, a first optical sensor for detecting first light based on reflection light reflected from the substrate, a second optical sensor for detecting second light based on the reflection light, a first spatial filter disposed between the first optical sensor and the substrate for transmitting the first light, and a second spatial filter disposed between the second optical sensor and the substrate for transmitting the second light. The first and second spatial filters have shapes that different from each other.

According to an exemplary embodiment of the inventive concept, an inspection apparatus includes a light source device for providing incident light to a substrate, an objective lens for transmitting reflection light reflected from the substrate, a light splitting device disposed over the objective lens for receiving the reflection light transmitted from the objective lens, the light splitting device for splitting the received reflection light into first and second split light, a first optical sensor disposed at one side of the light splitting device for detecting the first split light, a second optical sensor disposed at a second other side of the light splitting device for detecting the second split light, a first spatial filter disposed between the first optical sensor and the light splitting device, and a second spatial filter disposed between the second optical sensor and the light splitting device. The first spatial filter has a first aperture for transmitting the first split light. The second spatial filter has a second aperture for transmitting the second split light. The first and second apertures have shapes different from each other.

According to an exemplary embodiment of the inventive concept, a method of manufacturing a semiconductor device includes performing a manufacturing process on an $N^{th}$ substrate by a manufacturing apparatus, inspecting a top surface of the $N^{th}$ substrate by an inspection apparatus, and determining whether a defect pattern image obtained by the inspection exists or not. According to another exemplary embodiment of the inventive concept, a method of manufacturing the semiconductor device includes starting a manufacturing process for generating the semiconductor device; controlling an inspection apparatus to apply incident light to a top surface of a current substrate generated by the manufacturing process, split reflected light reflected from the top surface into first and second split light, and detect first and second images from the first and second split light; determining whether a defect is present in the current substrate based on a difference calculated between the first and second images; ending the manufacturing process when the defect is present; and continuing the manufacturing process on a subsequent substrate when the defect is not present.

According to an exemplary embodiment of the inventive concept, an apparatus configured to test a substrate includes: a light source device for providing incident light to the substrate; an objective lens for transmitting light reflected from the substrate in response to the incident light; a first mirror disposed over the objective lens for generating first split light from the reflection light; a second mirror disposed over the objective lens for generating second split light from the reflection light; a first optical sensor for detecting a first image from the first split light; a second optical sensor for detecting a second image from the second split light; a first spatial filter disposed between the first optical sensor and the mirrors; a second spatial filter disposed between the second optical sensor and the mirrors; and a controller configured to determine whether the substrate has a defect based on the first and second images. The first and second spatial filters have shapes that differ from one another.

BRIEF DESCRIPTION OF THE DRAWINGS

The inventive concepts will become more apparent in view of the attached drawings and accompanying detailed description.

DETAILED DESCRIPTION OF THE EMBODIMENTS

Figure 1:
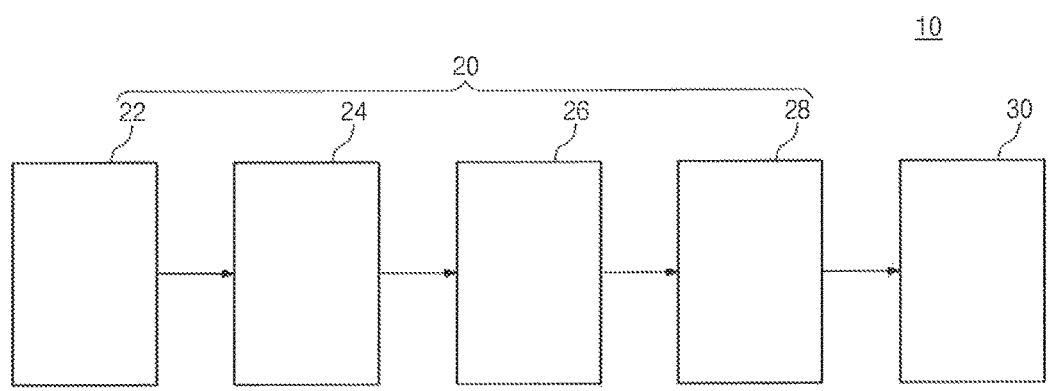
FIG. 1 is a block diagram illustrating a system of manufacturing a semiconductor device, according to an exemplary embodiment of the inventive concept.

FIG. 1 is a block diagram illustrating a system 10 of manufacturing a semiconductor device, according to an exemplary embodiment of the inventive concept.

Figure 10:
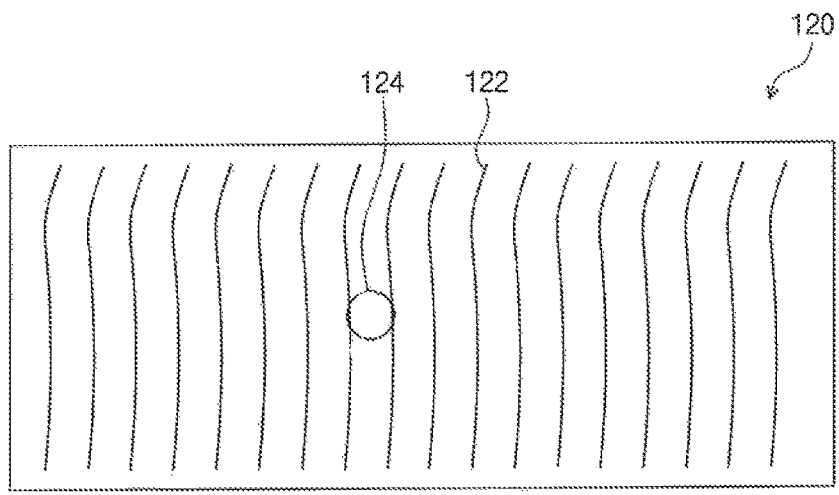
FIG. 10 is a view illustrating a second image detected from a second optical sensor of FIG. 2.

Referring to FIG. 10, a system 10 of manufacturing a semiconductor device includes a manufacturing apparatus 20 and an inspection apparatus 30. The manufacturing apparatus 20 performs a manufacturing process to manufacture substrate W of FIG. 2. The inspection apparatus 30 is used inspect the substrate W for defects. In an exemplary embodiment, the manufacturing apparatus 20 and the inspection apparatus 30 are arranged in a single row or column.

The manufacturing apparatus 20 may be disposed in front of the inspection apparatus 30. In an exemplary embodiment, the manufacturing apparatus 20 includes deposition equipment 22, photolithography equipment 24, etching equipment 26, and cleaning equipment 28. In an embodiment, the deposition equipment 22 performs a process of depositing a thin layer. In an embodiment, the photolithography equipment 24 performs a photolithography process. In an embodiment, the photolithography process is used to pattern parts of a thin film or the bulk of a substrate. For example, the photolithography process may be used to transfer a geometric pattern from a photomask to a light-sensitive chemical photoresist on the substrate. In an embodiment, the etching equipment 26 performs an etching process on the substrate. In an embodiment, the cleaning equipment 28 performs a cleaning process on the substrate. In an embodiment, equipment 22, 24, 26, and 28 of the manufacturing apparatus 20 is replaced with ion implantation equipment, diffusion equipment, thermal treatment equipment, and a stocker, respectively. In an embodiment, ion implantation is a materials engineering process by which ions of a material are accelerated in an electrical field and impacted into a solid.

In an exemplary embodiment, the inspection apparatus 30 inspects a top surface of the substrate W generated as a result of performing the manufacturing process. The inspection apparatus 30 may be disposed in the rear of the manufacturing apparatus 20. In an embodiment, the inspection apparatus 30 inspects a top surface of the substrate W while the manufacturing process is manufacturing the substrate W. For example, the inspection apparatus 30 may inspect the top surface before the manufacturing of the substrate has completed. In an embodiment, the inspection apparatus 30 is disposed within the manufacturing apparatus 20 so it can inspect the top surface of the substrate W while the substrate W is being manufactured. For example, the inspection apparatus 30 may be disposed between the deposition equipment 22 and the photolithography equipment 24 and/or between the photolithography equipment 24 and the etching equipment 26. The inspection apparatus 30 may inspect whether the manufacturing process is normal or not. For example, the inspection apparatus 30 may determine whether an error has occurred as a result of performing the manufacturing process. In an exemplary embodiment, the inspection apparatus 30 obtains information on a result of the manufacturing process.

Figure 2:
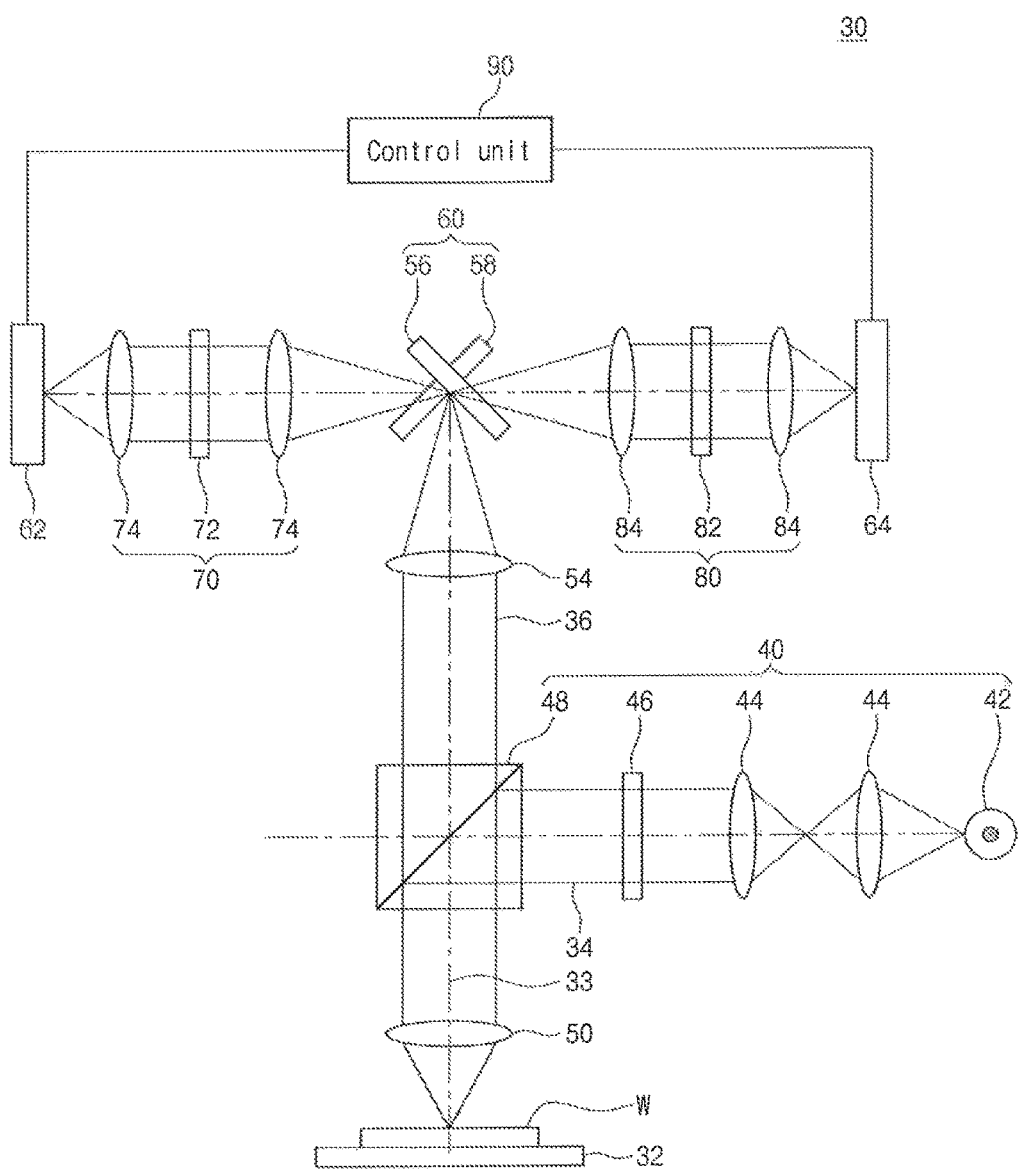
FIG. 2 is a view illustrating an inspection apparatus of FIG. 1 according to an exemplary embodiment of the inventive concepts.

FIG. 2 is a view illustrating the inspection apparatus 30 of FIG. 1 according to an exemplary embodiment of the inventive concept.

Referring to FIG. 2, the inspection apparatus 30 may include an optical inspection apparatus. In an exemplary embodiment, the inspection apparatus 30 includes a stage 32, a light source device 40, an objective lens 50, a light splitting device 60, first and second optical sensors 62 and 64, first and second imaging spatial filtering devices 70 and 80, and a control unit 90 (e.g., a controller, or controller device). In an embodiment, the stage 32 is omitted. In an embodiment, the objective lens 50 is transparent and performs a magnification operation. In an embodiment, one or more of the optical sensors 62 and 64 include a transceiver that enable them to wirelessly communicate with the control unit 90 and the control unit 90 also includes a transceiver that enables the control unit 90 to wirelessly receive these communications. For example, the transceiver may be used to wirelessly transmit images detected, sensed, or captured by the optical sensors 62 and 64.

The stage 32 receives the substrate W. For example, the substrate W may be loaded on top of the stage 32. The light source device 40 provides incident light 34 to a top surface of the substrate W loaded on the stage 32. The objective lens 50 receives and transmits reflection light 36 reflected from the substrate W. For example, when the incident light 34 is applied to the substrate W, the incident light 34 reflects off the surface of the substrate W to generate the reflection light 36. The light splitting device 60 splits the reflection light 36. The first and second optical sensors 62 and 64 detect the split reflection lights 36, respectively. The first and second imaging spatial filtering devices 70 and 80 transmit the split reflection lights 36 to the first and second optical sensors 62 and 64 in different forms from each other. For example, since the shapes of the filtering devices 70 and 80 differ from one another, they each filter their respectively received split reflection light in a different manner that results in different images being output to their respective optical sensors. The control unit 90 obtains a defect pattern image corresponding to a difference between the split reflection lights 36 transmitted from the first and second imaging spatial filtering devices 70 and 80.

The stage 32 may be disposed under the objective lens 50. In an embodiment, the stage 32 is configured to move the substrate W. In an embodiment, an actuator or a motor is used to move the substrate W. In an embodiment, the control unit 90 applies a signal to the actuator or motor to move the substrate W. The stage 32 may move the substrate W in a direction intersecting an optical axis 33 of the incident light 34 and the reflection light 36. For example, the stage 32 may move the substrate W in a direction perpendicular to the optical axis 33. Thus, the substrate W may be scanned by the incident light 34 and the reflection light 36.

The light source device 40 provides the incident light 34 to the objective lens 50. In an exemplary embodiment, the light source 40 includes a light source 42, illumination lenses 44, a light spatial filter 46, and a beam splitter 48. The light source 42 generates the incident light 34. The illumination lenses 44 are disposed between the light source 42 and the beam splitter 48. The illumination lenses 44 convert the incident light 34 generated from the light source 42 into a parallel light beam. The incident light 34 transmitted from the illumination lenses 44 is provided to the beam splitter 48. The light spatial filter 46 is disposed between the beam splitter 48 and the illumination lenses 44. The light spatial filter 46 may remove aberration of the incident light 34. Alternatively, the light spatial filter 46 may remove noise of the incident light 34. The beam splitter 48 may be aligned on or over the objective lens 50. The beam splitter 48 reflects the incident light 34 to the objective lens 50. The incident light 34 may be provided to the substrate W through the objective lens 50.

Figure 3:
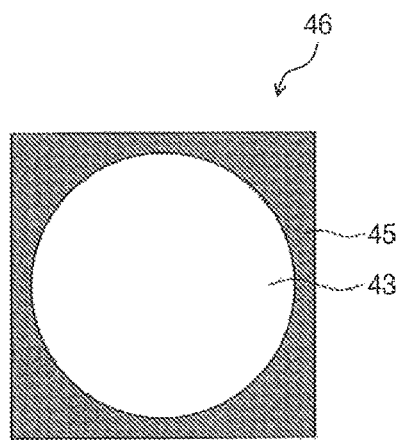
FIG. 3 is a plan view illustrating a light spatial filter of FIG. 2 according to an exemplary embodiment of the inventive concepts.

FIG. 3 is a plan view illustrating the light spatial filter 46 of FIG. 2 according to an exemplary embodiment of the inventive concept.

Referring to FIGS. 2 and 3, the light spatial filter 46 includes a first mask 45 having a first aperture 43. In an embodiment, the first aperture 43 is a circular through hole of the first mask 45. The first mask 45 may include chromium disposed on a transparent substrate. For example, the first mask 45 may have a regular quadrilateral shape. The first aperture 43 may be disposed in the first mask 45. In an exemplary embodiment, the first aperture 43 controls a beam size of the incident light 34. The first aperture 43 may determine a cross-sectional shape of the incident light 34. For example, the first aperture 43 may have a circular shape, and thus the cross section of the incident light 34 may have a circular shape.

Referring again to FIG. 2, the objective lens 50 is disposed over the substrate W. The objective lens 50 focuses the incident light 34 on the top surface of the substrate W. The incident light 34 is reflected by the top surface of the substrate W to generate the reflection light 34. The objective lens 50 receives and transmit the reflection light 36 to magnify the top surface of the substrate W. The magnification of the substrate W may be determined by a numeral aperture (NA) of the objective lens 50 and/or a wavelength of the incident light 34. The objective lens 50 may convert the reflection light 36 into a parallel light beam. The reflection light 36 may be transmitted through the beam splitter 48 so as to be provided to a tube lens 54. The tube lens 54 may provide the reflection light 36 to the light splitting unit 60, and the reflection light 36 may form an image in the light splitting unit 60.

The light splitting unit 60 may split the reflection light 36 toward the first and second optical sensors 62 and 64. In an exemplary embodiment, the light splitting unit 60 splits the reflection light 36 into two and reflects the two split reflection lights 36 toward the first and second optical sensors 62 and 64, respectively. For example, the light splitting unit 60 may include first and second dividing mirrors 56 and 58. The first and second dividing mirrors 56 and 58 may intersect the optical axis 33 of the reflection light 36. The first dividing mirror 56 reflects one of the two split reflection lights 36 toward the first optical sensor 62. The second dividing mirror 58 reflects the other of the two split reflection lights 36 toward the second optical sensor 64. Alternatively, the light splitting unit 60 may include a beam splitter. In an embodiment, the dividing mirrors 56 and 58 are disposed at acute angles relative to the optical axis 33. In an embodiment, the dividing mirrors 56 and 58 are disposed at angles that are perpendicular to one another. In an embodiment the dividing mirrors 56 and 58 transmit their respective split light at right angles relative to the optical axis 33.

The first and second optical sensors 62 and 64 are disposed at both sides of the light splitting unit 60, respectively. The first and second optical sensors 62 and 64 may obtain image data of the substrate W. For example, each of the first and second optical sensors 62 and 64 may include a charge-coupled device (CCD) image pickup device and/or a complementary metal-oxide-semiconductor (CMOS) image pickup device. For example, each of the optical sensors 62 may capture a magnified image of the top surface of the substrate W.

The first imaging spatial filtering device 70 is disposed between the light splitting device 60 and the first optical sensor 62. In an exemplary embodiment, the first imaging spatial filtering device 70 includes a first imaging spatial filter 72 and first relay lenses 74. The first imaging spatial filter 72 is disposed between the first relay lenses 74. The first imaging spatial filter 72 may remove aberration of one of the split reflection lights 36. Alternatively, the first imaging spatial filter 72 may remove noise of one of the split reflection lights 36. The first relay lenses 74 may extend a distance between the light splitting device 60 and the first optical sensor 62. One of the split reflection lights 36 may travel in parallel between the first relay lenses 74. Alternatively, the first relay lenses 74 may reverse an image of one of the split reflection lights 36.

Figure 4:
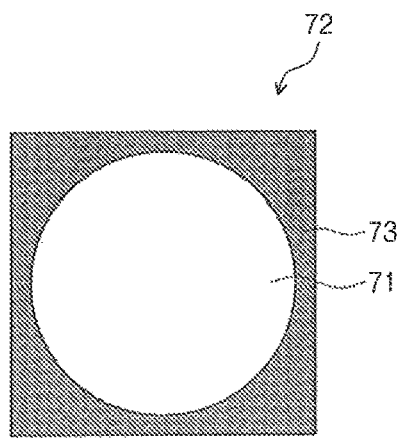
FIG. 4 is a plan view illustrating a first imaging spatial filter of FIG. 2 according to an exemplary embodiment of the inventive concept.

FIG. 4 is a plan view illustrating the first imaging spatial filter 72 of FIG. 2 according to an exemplary embodiment of the inventive concept.

Referring to FIG. 4, the first imaging spatial filter 72 includes a second mask 73 having a second aperture 71. In an embodiment, the second aperture 71 is a circular through hole of the second mask 73. For example, the second mask 73 may have a regular quadrilateral shape. The second aperture 71 may be disposed in the second mask 73. The second aperture 71 may control a beam size of the reflection light 36 between the light splitting device 60 and the first optical sensor 62. In an exemplary embodiment, the second aperture 71 has the same shape as the first aperture 43. For example, the second aperture 71 may have a circular shape. In an embodiment, a diameter of the first aperture 43 is the same as a diameter of the second aperture 71. A cross section of the reflection light 36 transmitted from the first imaging spatial filter 72 may have a circular shape. Alternatively, the second aperture 71 has a different shape from the first aperture 43. For example, the second mask 73 may include chromium disposed on a transparent substrate.

Figure 5:
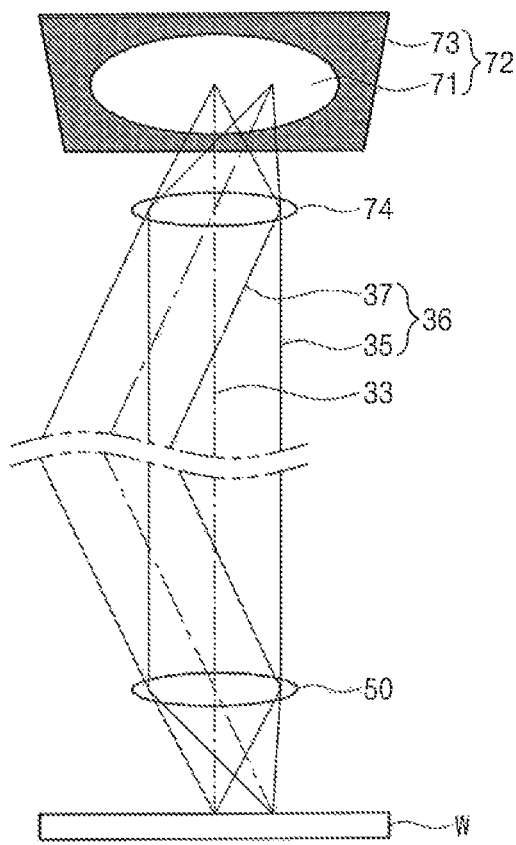
FIG. 5 is a view illustrating the first imaging spatial filter of FIG. 4 and reflection light.

FIG. 5 is a view illustrating the first imaging spatial filter 72 of FIG. 4 and the reflection light 36.

Referring to FIG. 5, the first imaging spatial filter 72 may control transmission and/or absorption of an angle component of the image of the reflection light 36 between the light splitting device 60 and the first optical sensor 62. In an exemplary embodiment, the reflection light 36 includes regular reflection light 35 and scattered reflection light 37. The regular reflection light 35 may be light reflected from the substrate W in a single direction. The regular reflection light 35 may have an incidence angle and a reflection angle which are equal to each other due to Snell's law. For example, the regular reflection light 35 may be reflected in a direction perpendicular to the top surface of the substrate W. The scattered reflection light 37 may be light reflected from the top surface of the substrate W at various angles. For example, the scattered reflection light 37 may be mainly generated at boundaries of patterns on the substrate W. The scattered reflection light 37 may be reflected in directions tilted with respect to the top surface of the substrate W.

In an exemplary embodiment, the regular reflection light 35 and the scattered reflection light 37 of the reflection light 36 pass through the second aperture 71 of the first imaging spatial filter 72. The regular reflection light 35 may be mainly provided to a center of the second aperture 71. The regular reflection light 35 may pass through the second aperture 71. The scattered reflection light 37 may be provided to an edge of the second aperture 71. The scattered reflection light 37 may pass through the second aperture 71. Thus, the first imaging spatial filter 72 may transmit both the regular reflection light 35 and the scattered reflection light 37 of the reflection light 36. Alternatively, the first imaging spatial filter 72 may selectively transmit one of the regular reflection light 35 and the scattered reflection light 37.

Referring back to FIG. 2, the second imaging spatial filter unit 80 is disposed between the light splitting device 60 and the second optical sensor 64. In an exemplary embodiment, the second imaging spatial filter 80 includes a second imaging spatial filter 82 and second relay lenses 84. The second imaging spatial filter 82 is disposed between the second relay lenses 84. The second imaging spatial filter 82 may remove aberration of the other of the split reflection lights 36. Alternatively, the second imaging spatial filter 82 may remove noise of the other of the split reflection lights 36. The second relay lenses 84 may extend a distance between the light splitting device 60 and the second optical sensor 64. The other of the split reflection lights 36 may travel in parallel between the second relay lenses 84. Alternatively, the second relay lenses 84 may reverse an image of the other of the split reflection lights 36.

Figure 6:
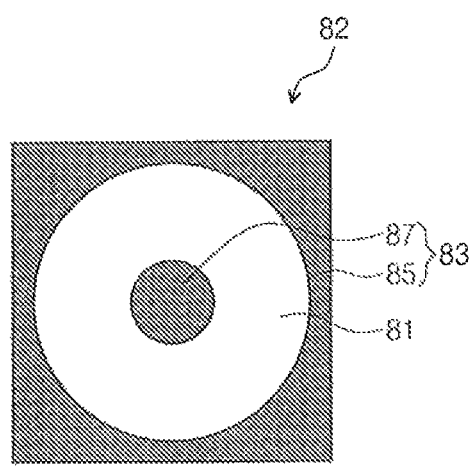
FIG. 6 is a plan view illustrating a second imaging spatial filter of FIG. 2 according to an exemplary embodiment of the inventive concept.

FIG. 6 is a plan view illustrating the second imaging spatial filter 82 of FIG. 2 according to an exemplary embodiment of the inventive concept.

Referring to FIG. 6, the second imaging spatial filter 82 includes a third mask 83 having a third aperture 81. The third aperture 81 may determine a beam size of the reflection light 36 between the light splitting unit 60 and the second optical sensor 64. In an exemplary embodiment, the third aperture 81 has a different shape from the first and second apertures 43 and 71. For example, the third aperture 81 may have a ring or an annulus shape. In an embodiment, an outer diameter of the third aperture 81 is equal to a diameter of the second aperture 71. In an exemplary embodiment, the third mask 83 includes an outer pattern 85 and an inner pattern 87. For example, the outer pattern 85 may have a regular quadrilateral shape. The third aperture 81 and the inner pattern 87 may be disposed in the outer pattern 85. In an embodiment, the outer diameter of the third aperture 81 is greater than the diameter of the inner pattern 87. In an embodiment, the area of the third aperture 81 is greater than the area of the inner pattern 87. The inner pattern 87 may be disposed in the third aperture 81. The inner pattern 87 may have a dark disk pattern shape smaller than the third aperture 81. The outer pattern 85 and the inner pattern 87 may include chromium disposed on a transparent substrate.

Figure 7:
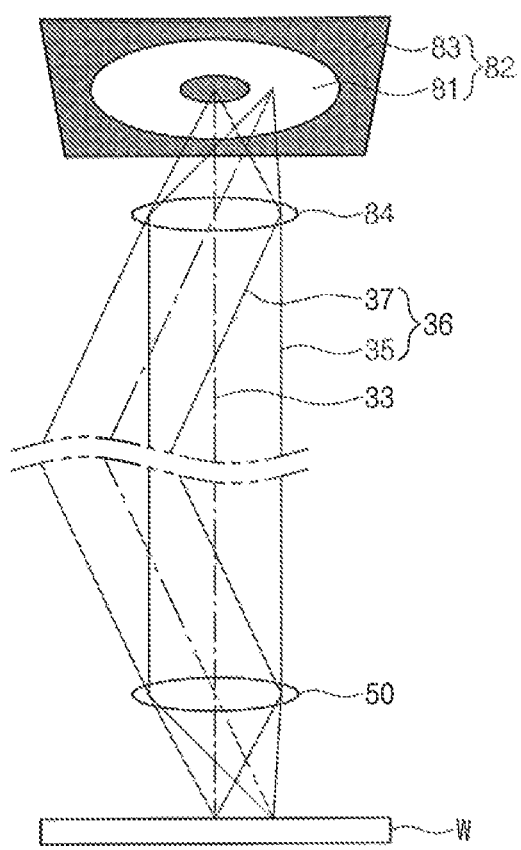
FIG. 7 is a view illustrating the second imaging spatial filter of FIG. 6 and reflection light.

FIG. 7 is a view illustrating the second imaging spatial filter 82 of FIG. 6 and the reflection light 36.

Referring to FIG. 7, the second imaging spatial filter 82 may control transmission and/or absorption of an angle component of the image of the reflection light 36 between the light splitting device 60 and the second optical sensor 64. In an exemplary embodiment, the second imaging spatial filter 82 absorbs the regular reflection light 35 of the reflection light 36 but transmits the scattered reflection light 37 of the reflection light 36. The regular reflection light 35 may be provided to the third mask 83 (i.e., the inner pattern 87 of FIG. 6) disposed at a central portion of the third aperture 81. The third mask 83 may absorb the regular reflection light 35. The scattered reflection light 37 may be provided to the third aperture 81. In other words, the third aperture 81 may transmit the scattered reflection light 37. Thus, in an exemplary embodiment, the second imaging spatial filter 82 removes the regular reflection light 35 and transmits the scattered reflection light 37.

Referring back to FIG. 2, the first and second optical sensors 62 and 64 may detect different images from the split reflection lights 36 respectively transmitted from the first and second imaging spatial filters 72 and 82. The first and second optical sensors 62 and 64 may detect the images at about the same time. Thus, the images may be detected by a single scan of the reflection light 36. In other words, the first and second optical sensors 62 and 64 may detect the images almost in real time.

The control unit 90 may obtain the images of the first and second optical sensors 62 and 64. In an embodiment, the control unit 90 compares the images with each other to obtain a difference image between the images. For example, a common part of the images may be removed. The difference image between the images may be a defect pattern image on the substrate W. Thus, the control unit 90 may obtain the defect pattern image in real time. In an embodiment, the control unit 90 includes a comparator to compare the images or a subtractor to obtain the difference image.

A method of obtaining the defect pattern image using the system 10 described above will be described below.

Figure 8:
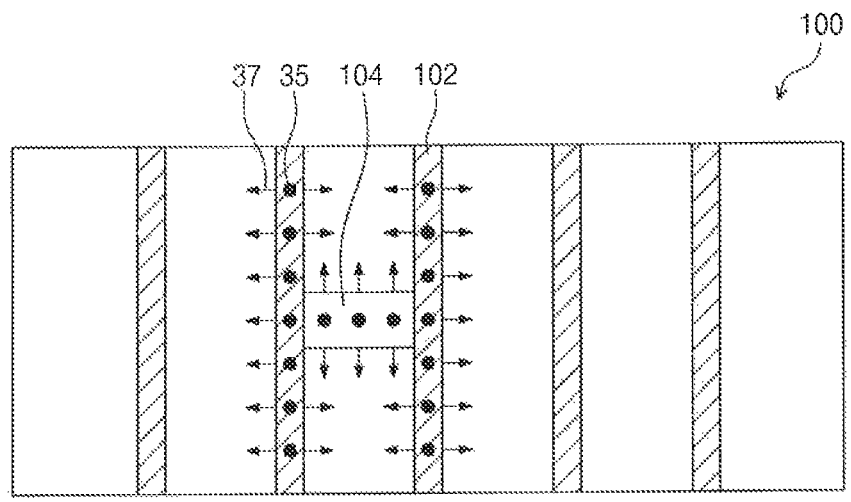
FIG. 8 is a plan view illustrating an embodiment of patterns formed on a substrate by a manufacturing apparatus of FIG. 1.

FIG. 8 is a plan view illustrating examples of patterns 100 that may be formed on a substrate W by the manufacturing apparatus 20 of FIG. 1.

Referring to FIG. 8, patterns 100 include normal patterns 102 and a defect pattern 104. For example, the normal patterns 102 may include metal interconnections. Alternatively, the normal patterns 102 may include polygonal blocks. Each of the normal patterns 102 may include a width of several nanometers (nm) to several tens of nm. The normal patterns 102 may be spaced apart from each other by a distance of several tens of nm to several hundreds of nm. The defect pattern 104 may be disposed between the normal patterns 102. For example, the defect pattern 104 may include a bridge pattern between the normal patterns 102. A width of the defect pattern 104 may be greater than that of each of the normal patterns 102. The defect pattern 104 may have a width of several tens of nm to several hundreds of nm. Alternatively, the defect pattern 104 may include a cut region of the metal interconnections and/or a short portion of the metal interconnections.

When the incident light 34 is provided to the normal patterns 102 and the defect pattern 104, each of the normal and defect patterns 102 and 104 may generate regular reflection light 35 and scattered reflection light 37. The regular reflection light 35 may travel in a direction perpendicular to each of the normal and defect patterns 102 and 104 (e.g., in a direction perpendicular to a top surface of a substrate W). In other words, FIG. 8 is a plan view and the regular reflection light 35 may travel like a vector that is normal to a surface of the plan view.

The scattered reflection light 37 may be mainly generated from an edge and/or a boundary of each of the normal and defect patterns 102 and 104. For example, the scattered reflection light 37 may travel around each of the normal and defect patterns 102 and 104.

Figure 9:
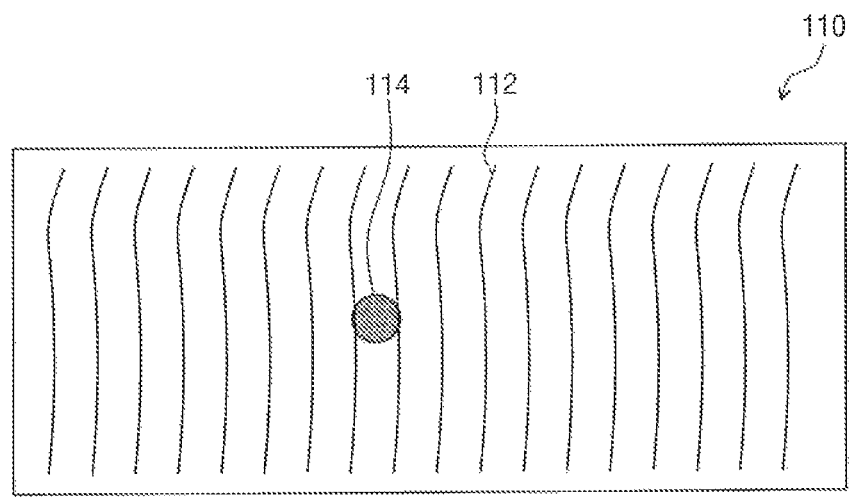
FIG. 9 is a view illustrating a first image detected from a first optical sensor of FIG. 2.

FIG. 9 is a view illustrating a first image 110 detected from the first optical sensor 62 of FIG. 2.

Referring to FIGS. 2, 5, and 9, the control unit 90 may obtain the first image 110 through the first optical sensor 62. In an exemplary embodiment, the first image 110 includes a first normal pattern image 112 and a first defect pattern image 114. The first normal pattern image 112 may be obtained from the regular reflection light 35 and the scattered reflection light 37 of the normal patterns 102. In an embodiment, wavelengths of the regular reflection light 35 and the scattered reflection light 37 are greater than the width of the normal patterns 102 and are similar to the distance between the normal patterns 102. The wavelengths of the regular reflection light 35 and the scattered reflection light 37 may range from about 400 nm to about 700 nm. Since the width of each of the normal patterns 102 is much smaller than a length of each of the normal patterns 102, the first normal pattern image 112 may show length-directional shapes of the normal patterns 102 regardless of width-directional shapes of the normal patterns 102. For example, the first normal pattern image 112 may include a stripe image. The first defect pattern image 114 may be obtained from the regular reflection light 35 and the scattered reflection light 37 of the defect pattern 104. The regular reflection light 35 and the scattered reflection light 37 of the defect pattern 104 may have wavelengths similar to the width of the defect pattern 104. For example, the first defect pattern image 114 may include a dark disk image and/or a block image.

FIG. 10 is a view illustrating a second image 120 detected from the second optical sensor 64 of FIG. 2.

Referring to FIGS. 2, 7, and 10, the control unit 90 may obtain a second image 120 through the second optical sensor 64. In an exemplary embodiment, the second image 120 includes a second normal pattern image 122 and a second defect pattern image 124. The second normal pattern image 122 may be similar to the first normal pattern image 112. Since the width of each of the normal patterns 102 is much smaller than the length of each of the normal patterns 102, the second normal pattern image 122 may show length-directional shapes of the normal patterns 102 regardless of width-directional shapes of the normal patterns 102. For example, the second normal pattern image 122 may include a stripe image. The second normal pattern image 122 may be obtained from the scattered reflection light 37 of the normal patterns 102. The regular reflection light 35 of the normal patterns 102 may be removed by the second imaging spatial filter 82. On the contrary, the scattered reflection light 37 of the normal patterns 102 may be detected as the second normal pattern image 122.

The second defect pattern image 124 may be different from the first defect pattern image 114. For example, the second defect pattern image 124 may include a first gray disk image. The regular reflection light 35 of the defect pattern 104 may be removed for the most part, and the second defect pattern image 124 may be obtained from the scattered reflection light 37 of the defect pattern 104. Brightness of the second defect pattern image 124 may be lower than that of the first defect pattern image 114. For example, the second defect pattern image 124 may appear lighter than the first defect pattern image 114. The second defect pattern image 124 may be more blurred than the first defect pattern image 114.

In an exemplary embodiment, when the defect pattern 104 is not present, the difference between the first image 110 and the second images 120 yields an image all of the same or substantially the same color (e.g., white) or brightness.

Figure 11:
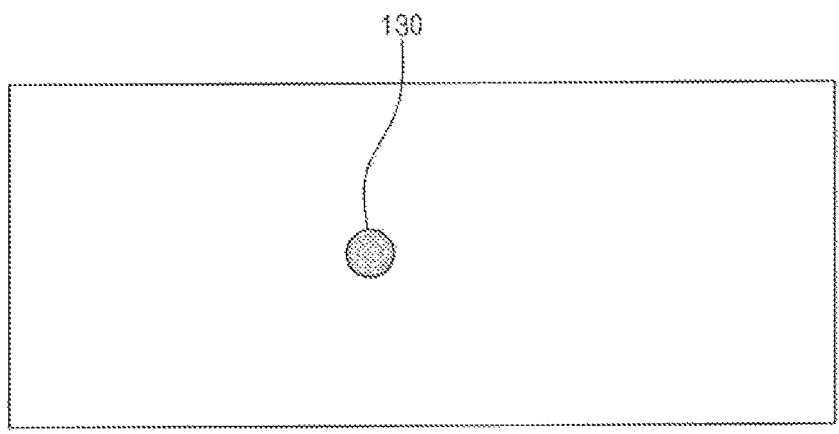
FIG. 11 is a view illustrating a defect pattern image corresponding to a difference image between the first image of FIG. 9 and the second image of FIG. 10.

FIG. 11 is a view illustrating a defect pattern image 130 corresponding to a difference image between the first image 110 of FIG. 9 and the second image 120 of FIG. 10.

Referring to FIGS. 2 and 9 to 11, the control unit 90 compares the first image 110 with the second image 120 to obtain a defect pattern image 130. The first normal pattern image 112 and the second normal pattern image 122 may correspond to a background image of the first image 110 and a background image of the second image 120, respectively.

The control unit 90 may remove the first normal pattern image 112 and the second normal pattern image 122. For example, the control unit 90 may include a subtractor to subtract the first image 110 from the second image 120 to cause the normal pattern images 112 and 122 to cancel out, which leaves only a visible difference between the defect pattern images 114 and 124.

The first defect pattern image 114 and the second defect pattern image 124 may correspond to the difference image between the first image 110 and the second image 120. The control unit 90 may obtain a defect pattern image 130. The defect pattern image 130 may correspond to a difference image between the first defect pattern image 114 and the second defect pattern image 124. In an exemplary embodiment, the defect pattern image 130 is more blurred than the first defect pattern image 114. For example, the defect pattern image 130 may include a second gray disk image. In an embodiment, the brightness of the defect pattern image 130 is greater than the brightness of the first defect pattern image 114 and less than the brightness of the second defect pattern image 124. The defect pattern image 130 may have information on the defect pattern 104 disposed on the top surface of the substrate W. When the defect pattern image 130 is obtained, the control unit 90 may decide that the manufacturing process is bad. For example, the control unit 90 may determine that an error has occurred during the manufacturing process when it detects the defect pattern image 130. The control unit 90 may be configured to notify one or more workers that the error has occurred during the manufacturing process. For example, the control unit 90 may include a display to present the error or be configured to send data over a network to a server that enables the server to present the error. On the contrary, when the defect pattern image 130 is not present, the control unit 90 may decide that the manufacturing process is normal (e.g., did not result in a defect pattern).

In an exemplary embodiment, the control unit 90 determines whether a defect pattern image is present based on a difference image between the images captured by the optical sensors 62 and 64 image. In an embodiment, the control unit 90 compares (e.g., using a comparator) the difference image against one or more reference images to determine whether the defect pattern image is present. For example, if the difference image differs from a reference image by less than a threshold amount, it is concluded that a defect pattern image is present and otherwise it is concluded that the defect pattern image is not present.

Figure 12:
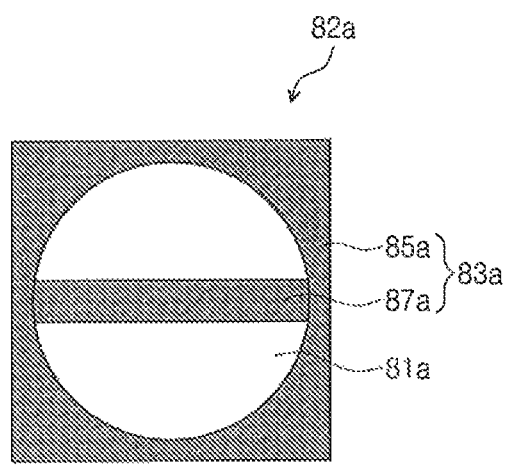
FIG. 12 is a plan view illustrating a second imaging spatial filter of FIG. 2 according to an exemplary embodiment of the inventive concept.

FIG. 12 is a plan view illustrating a second imaging spatial filter 82a according to an exemplary embodiment of the inventive concept. For example, the second imaging spatial filter 82 of FIG. 2 may be replaced with the second image spatial filter 82a of FIG. 12.

Referring to FIG. 12, the second imaging spatial filter 82a includes a third mask 83a having a third aperture 81a. The third aperture 81a has a circular shape having a horizontal center block. A diameter of the third aperture 81a may be equal to the second aperture 71. In an embodiment, the third aperture 81a has a circular shape having a vertical center block. For example, the third mask 83a may include an outer pattern 85a and an inner pattern 87a. The outer pattern 85a may have a regular quadrilateral shape. The third aperture 81a and the inner pattern 87a may be disposed in the outer pattern 85a. The third aperture 81a may have the circular shape. The inner pattern 87a may have a rectangular shape intersecting the third aperture 81a. In an exemplary embodiment, the inner pattern 87a intersects the third aperture 81a in a horizontal direction. In this embodiment, the inner pattern 87a corresponds to the horizontal center block. In an alternative embodiment, the inner pattern 87a intersects the third aperture 81a in a vertical direction. In this embodiment, the inner pattern 87a corresponds to the vertical center block.

Figure 13:
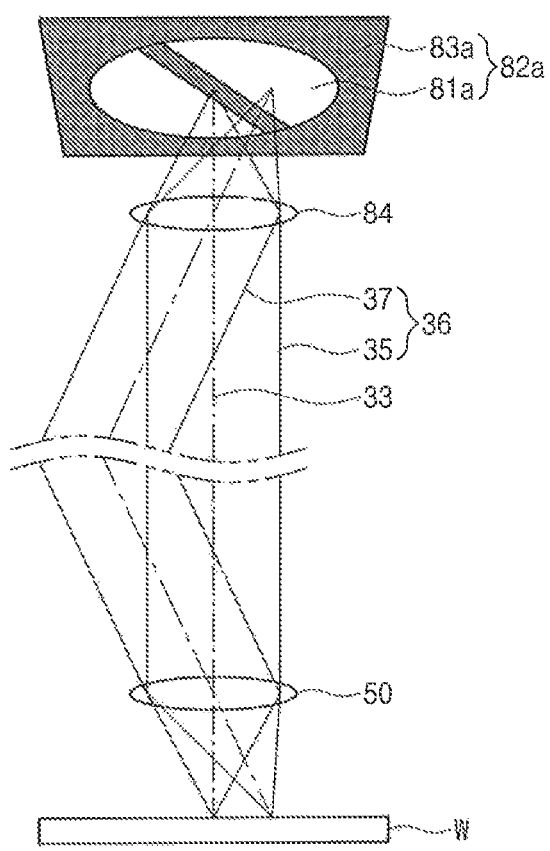
FIG. 13 is a view illustrating the second imaging spatial filter of FIG. 12 and reflection light.

FIG. 13 is a view illustrating the second imaging spatial filter 82a of FIG. 12 and reflection light 36.

Referring to FIG. 13, the second imaging spatial filter 82a may absorb the regular reflection light 35 and may transmit the scattered reflection light 37. In an embodiment, the regular reflection light 35 is absorbed by the third mask 83a (i.e., the outer pattern 85a and the inner pattern 87a of FIG. 12). In an embodiment, the scattered reflection light 37 passes through the third aperture 81a and under the inner pattern 87a.

Figure 14:
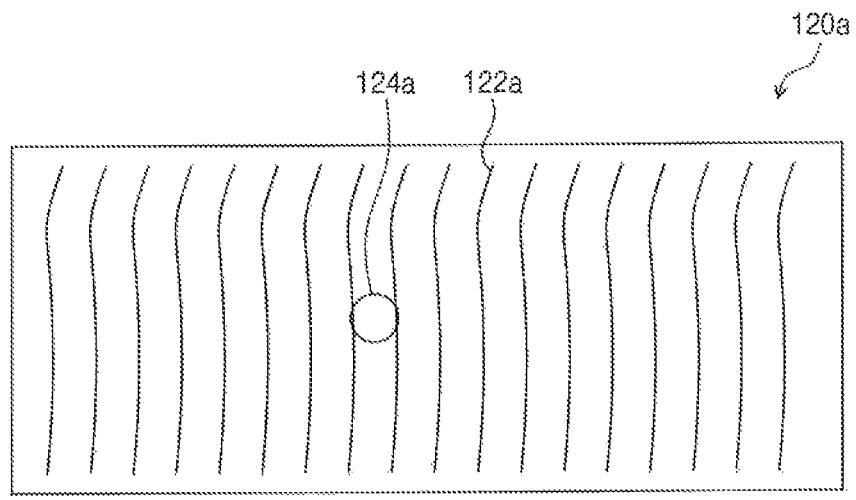
FIG. 14 is a view illustrating a second image detected from the second optical sensor of FIG. 2.

FIG. 14 is a view illustrating a second image 120a detected from the second optical sensor 64 of FIG. 2.

Referring to FIGS. 2, 13, and 14, the control unit 90 may obtain the second image 120a. For example, the second image 120a may include a second normal pattern image 122a of a stripe image and a second defect pattern image 124a of a circular image. The regular reflection light of the defect pattern 104 may be removed, and the second defect pattern image 124a may be obtained from the scattered reflection light 37 of the defect pattern 37. Thus, the second defect pattern image 124a may correspond to a contour of the defect pattern 104.

Figure 15:
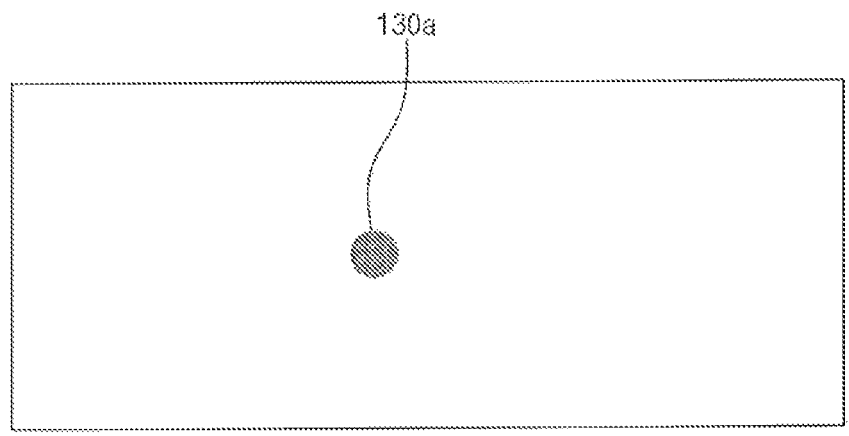
FIG. 15 is a view illustrating a defect pattern image corresponding to a difference image between the first image of FIG. 9 and the second image of FIG. 14.

FIG. 15 is a view illustrating a defect pattern image 130a corresponding to a difference image between the first image 110 of FIG. 9 and the second image 120a of FIG. 14.

Referring to FIGS. 2, 9, 14, and 15, the control unit 90 may obtain a defect pattern image 130a corresponding to a difference between the first defect pattern image 114 and the second defect pattern image 124a. In an exemplary embodiment, the defect pattern image 130a includes a second dark disk image. In an exemplary embodiment, the defect pattern image 130a is smaller than the first defect pattern image 114. In an exemplary embodiment, the defect pattern image 130a is more blurred than the first defect pattern image 114.

Figure 16:
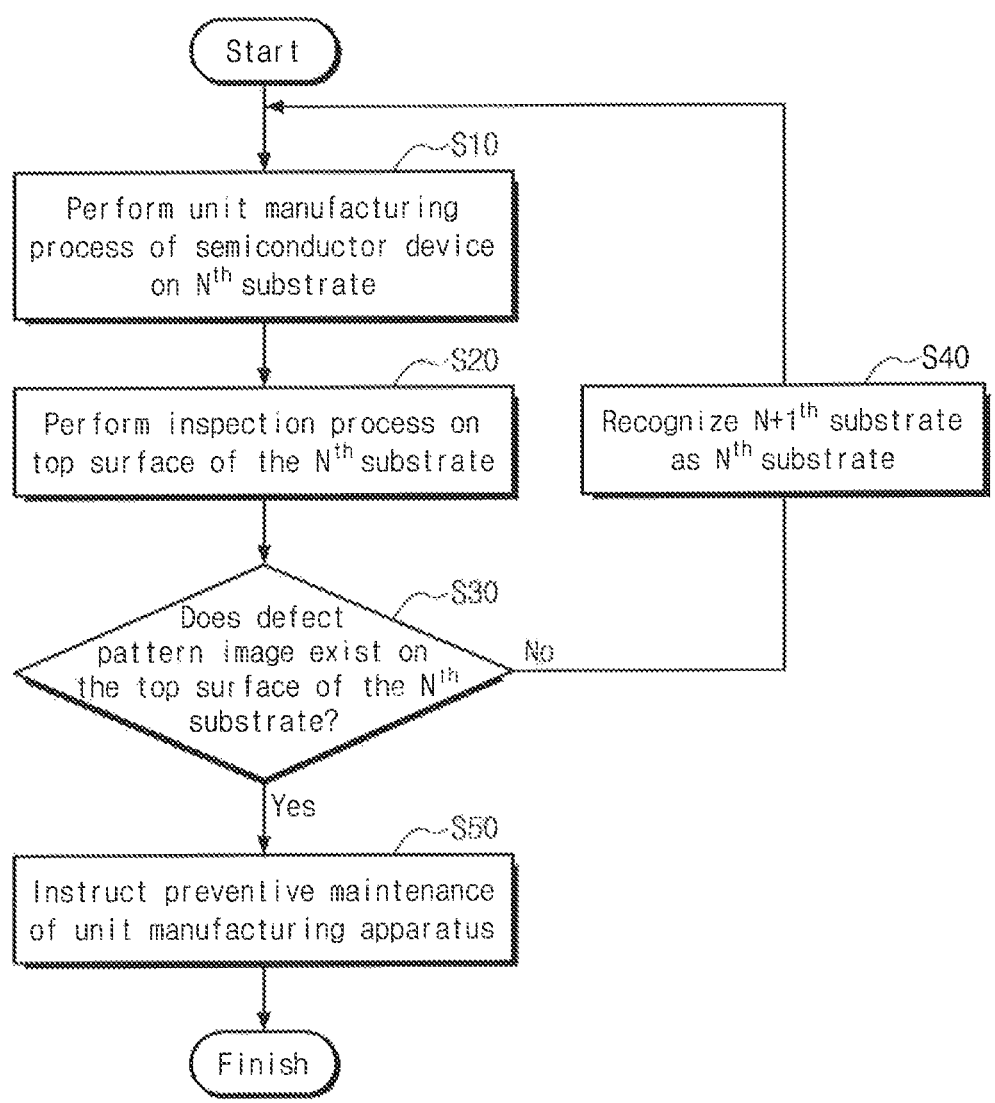
FIG. 16 is a flow chart illustrating a method of manufacturing a semiconductor device using the manufacturing system of FIG. 1, according to an exemplary embodiment of the inventive concept.

FIG. 16 is a flow chart illustrating a method of manufacturing a semiconductor device using the manufacturing system of FIG. 1, according to an exemplary embodiment of the inventive concept.

Referring to FIGS. 2, 8, and 16, the method of manufacturing a semiconductor device includes performing a unit manufacturing process of a semiconductor device on an $N^{th}$ substrate (S10), performing an inspection process (S20), and determining whether a defect pattern exists on a top surface of the $N^{th}$ substrate or not (S30). The performing of the unit manufacturing process may result in the forming of a semiconductor device or a part thereof. The determining of whether the defect pattern exists may be performed by the control unit 90 as described above. The method includes recognizing an $N+1^{th}$ substrate as the $N^{th}$ substrate (S40) if the defect pattern image does not exist and instructing preventive maintenance of the system 10 for manufacturing a semiconductor device when the defect pattern image exists (S50). For example, recognizing an $N+1^{th}$ substrate as the $N^{th}$ substrate means that steps S10-S30 will then be applied to the next substrate that is to be manufactured.

The manufacturing apparatus 20 may perform the unit manufacturing process of the semiconductor device on the $N^{th}$ substrate (S10).

The semiconductor device may include at least one of a dynamic random access memory (DRAM) device, a static random access memory (SRAM) device, an NAND flash memory device, or a three-dimensional (3D) NAND flash memory device. The unit manufacturing process may be a process of forming the patterns 100 on the $N^{th}$ substrate. For example, each of the patterns 100 may be a shallow trench isolation (STI) pattern, a word line, a gate stack, a spacer, a pad electrode, a contact hole, a bit line, a contact plug, a capacitor, or a metal line.

Referring to FIGS. 2, 9, 10, 11, and 16, the inspection apparatus 30 may perform the inspection process on the top surface of the $N^{th}$ substrate (S20). The inspection apparatus 30 may detect the first and second images 110 and 120 by using a single scan. The control unit 90 may obtain the defect pattern image 130. Thus, the control unit 90 may monitor the inspection process in real time.

When the defect pattern image 130 exists, the control unit 90 may instruct the preventive maintenance of the unit manufacturing apparatus 20 (S50). A worker may perform the preventive maintenance of the unit manufacturing apparatus 20. In an exemplary embodiment, a worker may perform the preventive maintenance of the inspection apparatus 30.

On the contrary, when the defect pattern image 130 does not exist, the control unit 90 may recognize an $N+1^{th}$ substrate as the $N^{th}$ substrate (S40) and then may perform a unit manufacturing process to generate a semiconductor device on the $N^{th}$ substrate (S10). The $N+1^{th}$ substrate may correspond to a substrate that is to be manufactured after the $N^{th}$ substrate. In other words, when the defect pattern image does not exist, a unit manufacturing process may be performed on the $N+1^{th}$ substrate subsequent to the $N^{th}$ substrate.

According to an exemplary embodiment of the inventive concept, the inspection apparatus includes first and second spatial filters providing reflection lights having different shapes to first and second optical sensors. The first and second optical sensors may respectively detect first and second images of the surface of a substrate by a single scan using the reflection light. A control unit of the inspection apparatus may obtain a defect pattern image corresponding to the difference between the first and second images.

According to an exemplary embodiment of the inventive concept, a method of manufacturing a semiconductor device is provided. The method includes: starting a manufacturing process for generating the semiconductor device; controlling an inspection apparatus (e.g., 30) to apply incident light to a top surface of a current substrate generated by the manufacturing process, split reflected light reflected from the top surface into first and second split light, and detect first and second images from the first and second split light; determining (e.g., by control unit 90) whether a defect is present in the current substrate based on a difference calculated between the first and second images; ending the manufacturing process when the defect is present; and continuing the manufacturing process on a subsequent substrate when the defect is not present.

While the inventive concept has been described with reference to exemplary embodiments, it will be apparent to those skilled in the art that various changes and modifications may be made without departing from the spirit and scope of the inventive concept. For example, the second aperture 71 of the first imaging spatial filter 72 may include a circular shape having the horizontal center block and/or the vertical center block. On the contrary, the third aperture 81 of the second imaging spatial filter 82 may have a circular shape or a ring shape. Therefore, it should be understood that the above embodiments are not limiting, but illustrative.

What is claimed is:

1. An inspection apparatus comprising:
   a light source device for providing incident light to a substrate;
   an objective lens for transmitting reflection light reflected from the substrate;
   a light splitting device disposed over the objective lens for receiving the reflection light transmitted from the objective lens, the light splitting device for splitting the received reflection light into a first split light and a second split light;
   a tube lens disposed between the objective lens and the light splitting device;
   a first optical sensor disposed at one side of the light splitting device for detecting the first split light;
   a second optical sensor disposed at a second other side of the light splitting device for detecting the second split light;
   a first spatial filtering device disposed between the first optical sensor and the light splitting device, the first spatial filter device comprising a first spatial filter; and
   a second spatial filtering device disposed between the second optical sensor and the light splitting device, the second spatial filtering device comprising a second spatial filter,
   wherein the first and second spatial filters have shapes that differ from one another,
   wherein the first split light travels in a first direction towards the first optical sensor and the second split light travels in a second direction opposing the first direction towards the second optical sensor,
   wherein the light splitting device comprises:
      a first dividing mirror reflecting the reflection light received from the tube lens toward the first optical sensor; and
      a second dividing mirror reflecting the reflection light received from the tube lens toward the second optical sensor,
      wherein the first and second dividing mirrors intersect in an X-shape and have an intersecting point, and
      wherein the intersecting point is disposed in an optical axis of the tube lens and a focus point of the tube lens.

2. The inspection apparatus of claim 1, wherein the first spatial filter includes a first mask having a first aperture for transmitting the first split light,
   wherein the second spatial filter includes a second mask having a second aperture for transmitting the second split light,
   wherein the first and second apertures have shapes different from each other.

3. The inspection apparatus of claim 2, wherein the first aperture has a circular shape, and
   wherein the second aperture has a ring shape of which an outer diameter is equal to a diameter of the first aperture.

4. The inspection apparatus of claim 2, wherein the first aperture has a circular shape,
   wherein the second aperture has a circular shape having a center block, and
   wherein a diameter of the second aperture is equal to a diameter of the first aperture.

5. The inspection apparatus of claim 1, wherein the light source device comprises:
   a light source generating the incident light;
   a beam splitter disposed between the light source and the objective lens; and
   a third spatial filter disposed between the beam splitter and the light source.

6. The inspection apparatus of claim 5, wherein the third spatial filter has a third aperture for controlling a beam size of the incident light.

7. The inspection apparatus of claim 5, wherein the light source device further comprises illumination lenses disposed between the light source and the third spatial filter.

8. The inspection apparatus of claim 1, wherein the first spatial filtering device further comprises a first relay lens disposed between the first optical sensor and the first spatial filter and a second relay lens disposed between the first spatial filter and the light splitting device, and
wherein the second spatial filtering device further comprises a third relay lens disposed between the second optical sensor and the second spatial filter and a fourth relay lens disposed between the second spatial filter and the light splitting device.

9. A system for manufacturing a semiconductor device, the system comprising:
a manufacturing apparatus for performing a manufacturing process on a substrate to generate a semiconductor device; and
an inspection apparatus spaced apart from the manufacturing apparatus, the inspection apparatus for inspecting the substrate,
wherein the inspection apparatus comprises:
a light source device for providing incident light to the substrate;
an objective lens for transmitting reflection light reflected from the substrate;
a light splitting device disposed over the objective lens and for receiving the reflection light transmitted from the objective lens, the light splitting device for splitting the received reflection light into a first split light and a second split light;
a tube lens disposed between the objective lens and the light splitting device:
a first optical sensor disposed at one side of the light splitting device for detecting the first split light;
a second optical sensor disposed at a second other side of the light splitting device for detecting the second split light;
a first spatial filtering device disposed between the first optical sensor and the light splitting device, the first spatial filtering device comprising a first spatial filter; and
a second spatial filtering device disposed between the second optical sensor and the light splitting device, the second spatial filtering device comprising a second spatial filter,
wherein the first and second spatial filters have shapes that differ from one another, and
wherein the first split light travels in a first direction towards the first optical sensor and the second split light travels in a second direction opposing the first direction towards the second optical sensor,
wherein the light splitting device comprises:
a first dividing mirror reflecting the reflection light received from the tube lens toward the first optical sensor; and
a second dividing mirror reflecting the reflection light received from the tube lens toward the second optical sensor,
wherein the first and second dividing mirrors intersect in an X-shape and have an intersecting point, and
wherein the intersecting point is disposed in an optical axis of the tube lens and a focus point of the tube lens.

10. The system of claim 9, wherein the inspection apparatus further comprises a controller for comparing a first image detected by the first optical sensor with a second image detected by the second optical sensor to obtain a defect pattern image.

11. The system of claim 10, wherein the first image includes a first normal pattern image and a first defect pattern image,
wherein the second image includes a second normal pattern image and a second defect pattern image, and
wherein the controller obtains the defect pattern image from a difference between the first defect pattern image and the second defect pattern image.

12. The system of claim 11, wherein the first defect pattern image includes a first disk shaped image of a first brightness,
wherein the second defect pattern image includes a second disk shaped image of a second brightness, and
wherein the defect pattern image obtained by the controller is a third disk shaped image corresponding to a brightness difference between the first brightness and the second brightness.

13. The system of claim 11, wherein the first defect pattern image includes a first disk shaped image,
wherein the second defect pattern image includes a circular image, and
wherein the defect pattern image obtained by the controller is a second disk shaped image smaller than the first disk shaped image.

14. An inspection apparatus comprising:
a light source device for providing incident light to a substrate;
a first optical sensor for detecting first light based on reflection light reflected from the substrate;
a second optical sensor for detecting second light based on the reflection light reflected from the substrate;
a first spatial filter disposed between the first optical sensor and the substrate for transmitting the first light;
a second spatial filter disposed between the second optical sensor and the substrate for transmitting the second light;
a light splitting device comprising a first dividing mirror reflecting the reflection light to generate the first light directed toward the first optical sensor and a second dividing mirror perpendicular to the first dividing mirror for reflecting the reflection light to generate the second light directed toward the second optical sensor;
a tube lens disposed between the light source and the light splitting device,
wherein the first and second spatial filters have shapes that differ from one another,
wherein the light splitting device comprises:
a first dividing mirror reflecting the reflection light received from the tube lens toward the first optical sensor; and
a second dividing mirror reflecting the reflection light received from the tube lens toward the second optical sensor,
wherein the first and second dividing mirrors intersect in an X-shape and have an intersecting point, and
wherein the intersecting point is disposed in an optical axis of the tube lens and a focus point of the tube lens.

15. The inspection apparatus of claim 14, further comprising:
an objective lens for providing the incident light to a top surface of the substrate and transmitting the reflection light, wherein the light splitting device is disposed over the objective lens and receives the reflection light transmitted from the objective lens.

16. The inspection apparatus of claim 14, wherein the first spatial filter includes a first mask having a first aperture for transmitting the first light, wherein the second spatial filter includes a second mask having a second aperture for transmitting the second light, and wherein the first and second apertures have shapes different from each other.

17. The inspection apparatus of claim 16, wherein the first aperture has a circular shape, and wherein the second aperture has a ring shape of which an outer diameter is equal to a diameter of the first aperture.

18. The inspection apparatus of claim 16, wherein the first aperture has a circular shape, wherein the second aperture has a circular shape having a center block, and wherein a diameter of the second aperture is equal to a diameter of the first aperture.

* * * * *